(12) United States Patent
Biedermann et al.

(10) Patent No.: US 9,186,192 B2
(45) Date of Patent: Nov. 17, 2015

(54) INSTRUMENT FOR INSERTING A BONE ANCHORING ELEMENT AND SYSTEM OF SUCH AN INSTRUMENT AND A POLYAXIAL BONE ANCHORING ELEMENT

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weiswell (DE); Dimosthenis Dandanopoulos, VS-Schwenningen (DE); Nicole Ruff, Deisslingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 77 days.

(21) Appl. No.: 14/194,319

(22) Filed: Feb. 28, 2014

(65) Prior Publication Data

US 2014/0249532 A1 Sep. 4, 2014

Related U.S. Application Data

(60) Provisional application No. 61/771,478, filed on Oct. 31, 2013.

(30) Foreign Application Priority Data

Mar. 1, 2013 (EP) .................................... 13157405

(51) Int. Cl.
*A61B 17/88* (2006.01)
*A61B 17/86* (2006.01)
(Continued)

(52) U.S. Cl.
CPC ................ *A61B 17/88* (2013.01); *A61B 17/16* (2013.01); *A61B 17/1671* (2013.01); *A61B 17/7037* (2013.01); *A61B 17/7076* (2013.01); *A61B 17/8875* (2013.01); *A61B 17/8886* (2013.01); *A61B 17/8888* (2013.01); *A61B 17/8891* (2013.01); *A61B 2017/1602* (2013.01)

(58) Field of Classification Search
CPC ........... A61B 17/16; A61B 2017/1602; A61B 17/1671; A61B 17/88; A61B 17/8875; A61B 17/8886; A61B 17/8888; A61B 17/8891
See application file for complete search history.

(56) References Cited

U.S. PATENT DOCUMENTS 4,640,271 A 2/1987 Lower
6,015,411 A * 1/2000 Ohkoshi et al. ................. 606/80
(Continued)

FOREIGN PATENT DOCUMENTS

WO WO 2011/068516 A1 6/2011

OTHER PUBLICATIONS

Extended European Search Report for European Application No. 13157405.5, European Search Report dated Jul. 24, 2013 and mailed Aug. 1, 2013 (7 pgs.).

*Primary Examiner* — Larry E Waggle, Jr.
(74) *Attorney, Agent, or Firm* — Christie, Parker & Hale, LLP

(57) ABSTRACT

An instrument for inserting a bone anchoring element into a bone is provided, the instrument including a shaft (2) having an end portion (23, 23') for engaging the bone anchoring element and for transferring torque to the bone anchoring element (1, 1') and a longitudinal axis defining an axis of rotation (R);
a cutting member (4, 4') connected to the shaft (2) with cutting portions (45) that are configured to cut bone material;
wherein the cutting member (4, 4') has an outer diameter (D) defined by the cutting portions (45) that is substantially the same or larger than an outer diameter (dd) of a receiving part (500) of the polyaxial bone anchor in a region at a bottom end (500b) of the receiving part.

20 Claims, 8 Drawing Sheets

(51) Int. Cl.
*A61B 17/16* (2006.01)
*A61B 17/70* (2006.01)

(56) References Cited

U.S. PATENT DOCUMENTS

| | | |
|---|---|---|
| 6,443,956 B1 | 9/2002 | Ray |
| 7,160,305 B2 * | 1/2007 | Schmieding .................... 606/80 |
| 8,029,509 B2 | 10/2011 | Ducharme |
| 2006/0064099 A1 | 3/2006 | Pavlov et al. |
| 2008/0306537 A1 | 12/2008 | Culbert |
| 2009/0187220 A1 | 7/2009 | Hamada |
| 2010/0234902 A1 | 9/2010 | Biedermann et al. |
| 2011/0004251 A1 | 1/2011 | Sweeney et al. |

* cited by examiner

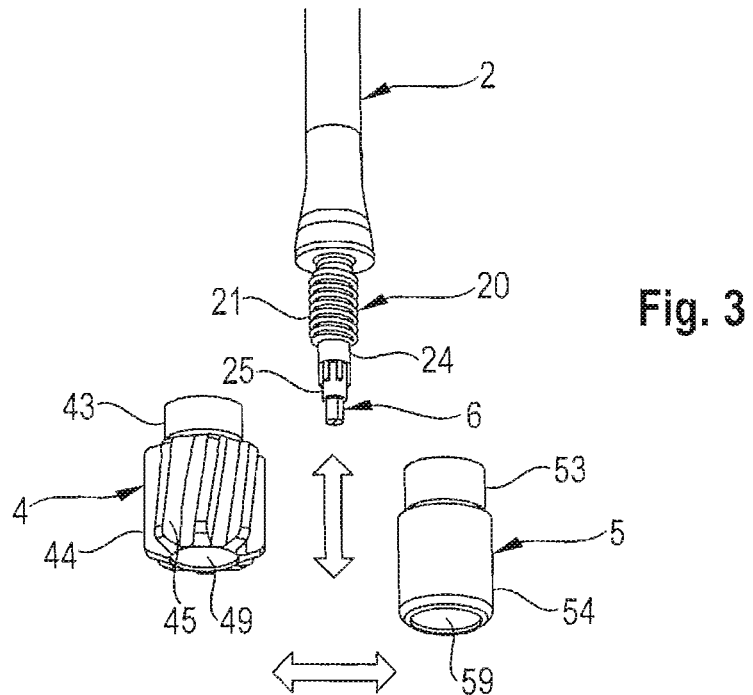
Fig. 3
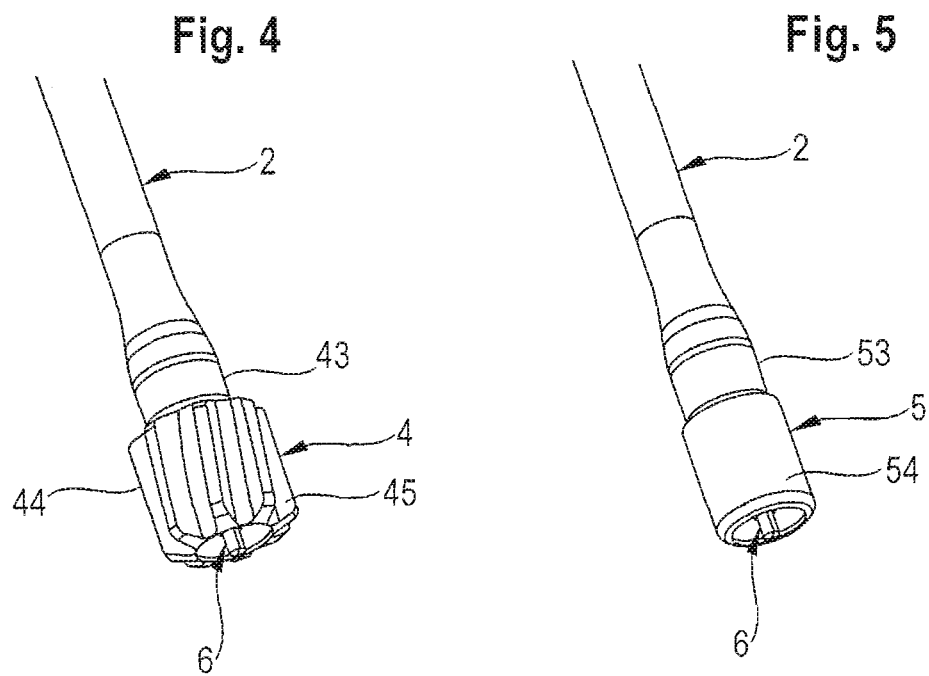
Fig. 4
Fig. 5

INSTRUMENT FOR INSERTING A BONE ANCHORING ELEMENT AND SYSTEM OF SUCH AN INSTRUMENT AND A POLYAXIAL BONE ANCHORING ELEMENT

CROSS-REFERENCE TO RELATED APPLICATION(S)

The present application claims priority to and the benefit of U.S. Provisional Patent Application Ser. No. 61/771,478, filed Mar. 1, 2013, the contents of which are hereby incorporated by reference in their entirety, and claims priority from European Patent Application EP 13 157 405.5, filed Mar. 1, 2013, the contents of which are hereby incorporated by reference in their entirety.

BACKGROUND

1. Field

The invention relates to an instrument for inserting a bone anchoring element into a bone or a vertebra, wherein the instrument has a cutting member for cutting bone material surrounding the implantation site. Further the invention relates to a system of such an instrument and a bone anchoring element and in particular to a system of such an instrument and a polyaxial bone anchor. The instrument includes a shaft with an end portion for engaging the anchoring element and a cutting member connected to the shaft. The cutting member comprises an outer diameter that is substantially the same or larger than an outer diameter of a receiving part of a polyaxial bone anchor, such that the cutting member can cut bone material to provide the necessary space for the receiving part to be mounted after the bone anchoring element has been inserted into the bone. The instrument is particularly useful together with a bottom loading type polyaxial pedicle screw.

2. Description of Related Art

Various inserting instruments for inserting a screw member of a polyaxial pedicle screw are known. For example, U.S. Pat. No. 6,443,956 B1 describes a vertebral drill bit for forming a pathway through a pedicle into a vertebral body. The vertebral drill bit includes a cutting shank having a generally uniform diameter, an attachment head at one end of the cutting shank and a tip at the other end of the cutting shank. A flute is formed in the cutting shank. With the instrument, a hole is drilled through a pedicle in which the screw member a polyaxial pedicle screw can be inserted later. The cutting shank flares proximate to the attachment head to substantially match the diameter thereof. This flared portion and the corresponding flared portion of a sharp edge of the flute form a countersink in the cortical bone to receive an integral nut of conventional screws.

A drill which is adapted to impact and provide a countersink for a bone for orthopedic surgery is known from U.S. Pat. No. 8,029,509 B2. The drill has a head that has a modified egg shape and a plurality of cutting flutes. The drill is designed specifically to provide a countersink in the cortical bone at the implantation site so that a round headed screw or peg will not remain proud or project too far beyond the surface of the bone.

WO 2011/068516 A1 describes a base reamer to be used in connection with an implanted pedicle screw. A particular base reamer is selected to correspond to the specific implant base that will be implanted in a given pedicle.

Recently, bottom loading type polyaxial bone anchors, such as a polyaxial bone anchor known from US 2010/0234902 A1, have been utilized in such a manner that the bone anchoring element is inserted into the bone first and after insertion the receiving part is mounted to the head of the bone anchoring element. This is advantageous in certain applications in which the insertion of the polyaxial bone anchoring device consisting of the pre-assembled anchoring element and the receiving part is too difficult, for example, because of limited space or restricted accessibility of the implantation site.

When mounting the receiving part "in-situ" onto the head of the bone anchoring element, a problem might occur in that there is not enough space around the head of the bone anchoring element for placing the receiving part onto the head or for pivoting the receiving part relative to bone anchoring element.

SUMMARY

It is the object of the invention to provide an instrument that facilitates and shortens the implanting step of a bone anchoring element, in particular in connection with the use of polyaxial bone anchors and more particularly in connection with the use of bottom loading type polyaxial bone anchoring devices. Furthermore, a system of such an instrument and a bone anchoring element and also a system of such an instrument and a polyaxial bone anchor shall be provided.

The object is solved by an instrument according to claim 1, a system according to claim 13 and a system according to claim 15. Further developments are given in the dependent claims.

With the instrument it is possible to simultaneously insert the bone anchoring element into the bone and to cut material in the surroundings of the insertion site to allow the in-situ mounting of the receiving part onto the head of the bone anchoring element after insertion of the anchoring element. Therefore, a separate step of cutting the surrounding bone material or base reaming after insertion of the bone anchoring element is no longer needed. Hence, the surgical procedure can be shortened. The time saving may be considerable in the case of a plurality of bone anchoring devices that have to be inserted, for example, in the case of correcting scoliosis.

Using the instrument, an optimized position of the head of the bone anchoring element for mounting a receiving part of a polyaxial bone anchor can be achieved.

The instrument can be used instead of the cutting member with a holding sleeve that can be mounted to the shaft of the instrument. Therefore, if the specific situation does not require the cutting of bone material, the instrument can be used with the holding sleeve as an insertion instrument without cutting bone material. The holding sleeve has a smaller outer diameter than the cutting member, so that the instrument can be applied to insert the bone anchoring element if the space around the implantation site is restricted and cutting or reaming is either not necessary or performed in a separate step.

The instrument and the bone anchoring element are connected in such a way, for example through a retaining element, that the bone anchoring element is aligned with the instrument in a straight position and firmly held by the instrument. This facilitates the insertion of the bone anchoring element and prevents wobbling of the anchoring element.

BRIEF DESCRIPTION OF THE DRAWINGS

Further features and advantages of the invention will be come apparent from the description of embodiments by means of the accompanying drawings. In the drawings:

FIG. 3 shows a schematic perspective view showing a front portion of the instrument and the cutting member and a holding sleeve which can be mounted to the shaft of the instrument in an exchangeable manner;

FIG. 4 shows a perspective view of an enlarged front portion of the instrument with the cutting member mounted thereto;

FIG. 5 shows a perspective view of an enlarged front portion of the instrument with the holding sleeve mounted thereto;

DETAILED DESCRIPTION

Figure 1:
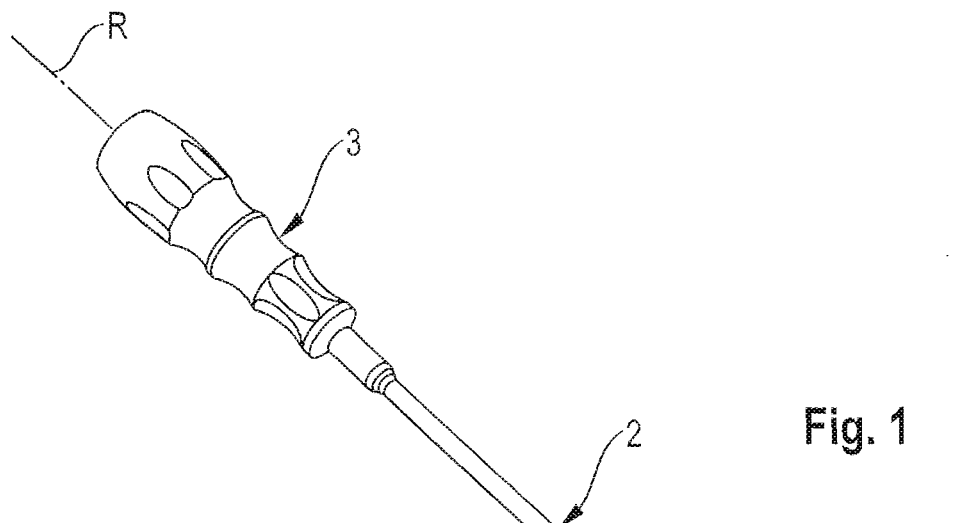
FIG. 1 shows a perspective view of the instrument with a cutting member attached to a bone screw.
Figure 2:
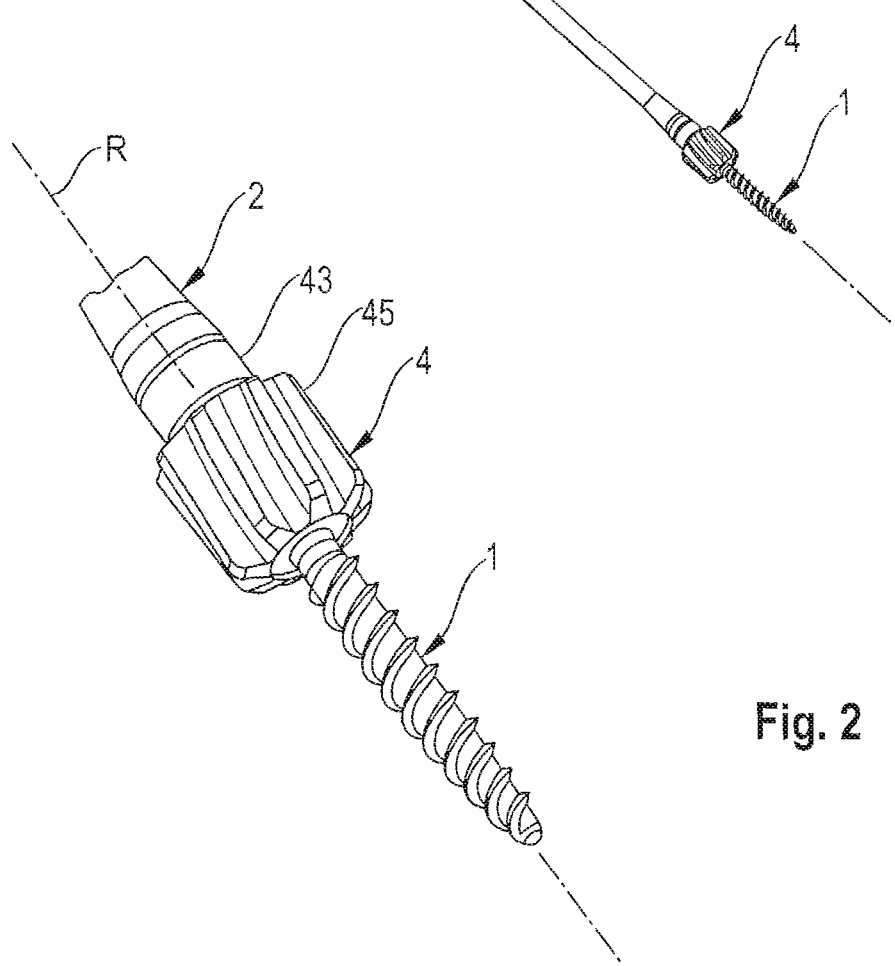
FIG. 2 shows a perspective view of an enlarged portion of the instrument with the cutting member attached to a bone screw.

Referring to FIGS. 1 and 2, an instrument for inserting a bone anchoring element 1 into a bone or vertebra comprises a central shaft portion 2 with a handle 3 at one end and a cutting member 4 at the opposite end. A central longitudinal axis of the central shaft portion 2 defines an axis of rotation R of the instrument.

Referring to FIGS. 3 to 5, the cutting member 4 is connectable to a front portion 20 extending from the central shaft portion 2 at the end opposite to the handle 3. A holding sleeve 5 is further provided that can be connected to the front portion 20 of the shaft portion 2 instead of the cutting member 4. Hence, the cutting member 4 and the holding sleeve 5 are connectable to the shaft portion 2 in an interchangeable manner.

Figure 6:
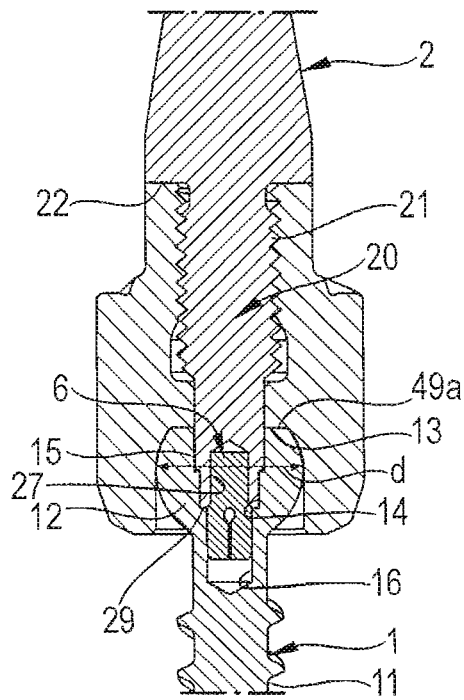
FIG. 6 shows a cross-sectional view of a front portion of the instrument with the cutting member mounted to the bone screw, the cross-section taken in a plane containing the central longitudinal axis of the shaft of the instrument and of the bone screw.
Figure 7:
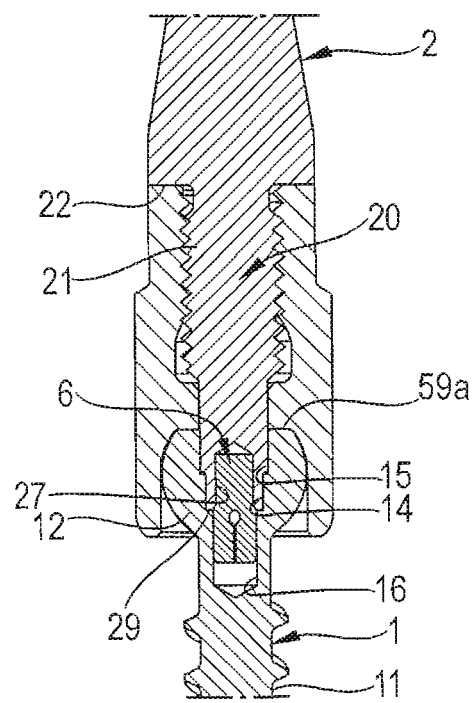
FIG. 7 shows a cross-sectional view of a front portion of the instrument with the holding sleeve mounted to the bone screw, the cross-section taken in a plane containing the central longitudinal axis of the shaft of the instrument and of the bone screw.

As can be seen in particular in FIGS. 6 and 7, the bone anchoring element 1 is in one embodiment a bone screw having a threaded shank 11 and a head 12 that is a spherical segment-shaped head with a free end surface 13 and a largest outer diameter d. A coaxial recess 14 extends from the free end surface 13 into the head 12. The inner wall of the recess 14 may have an engagement structure 15, for example in the form of longitudinally extending grooves 15 for engagement with a portion of the instrument. From the bottom of the coaxial recess 14, a blind hole 16 extends deeper into the head and into the threaded shank 11 of the bone screw 1 which serves for accommodation of a connection element of the instrument described below.

Figure 8:
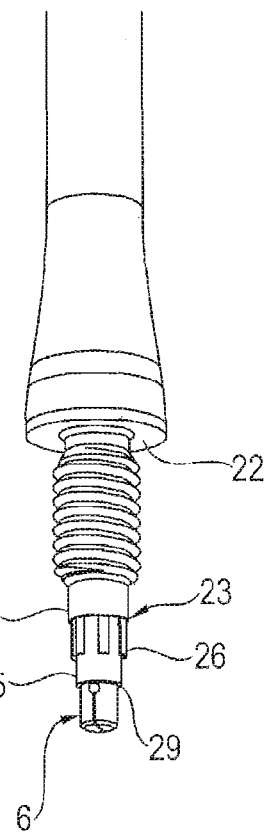
FIG. 8 shows a perspective view of the front portion of the shaft of the instrument to which a slotted pin is connected.
Figure 9:
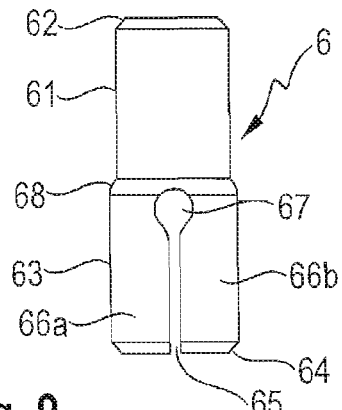
FIG. 9 shows an enlarged side view of the slotted pin shown in FIG. 8.
Figure 10:
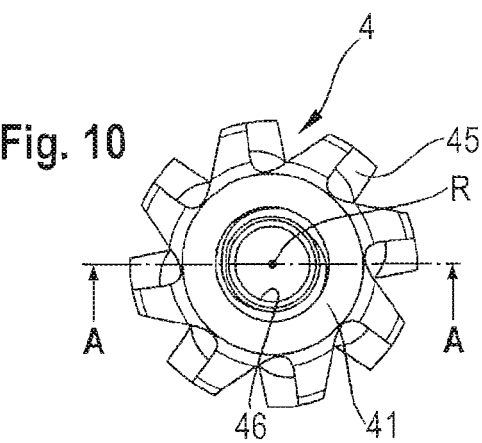
FIG. 10 shows a top view of the cutting member.

Referring further to FIGS. 8 and 9, the front portion 20 of the instrument comprises near to the end of the central shaft portion 2 a threaded section 21 with an external thread that is configured to cooperate with the cutting member 4 and the holding sleeve 5, respectively. The outer diameter of the threaded section 21 is generally smaller than the outer diameter of the central shaft portion 2, such that a stop surface 22 is formed at the end of the central shaft portion 2. Adjacent to the threaded portion 21 in the direction to a free end 29, the instrument comprises an anchoring element engagement portion 23 that consists of a first cylindrical portion 24 with an external diameter smaller than the external diameter of the threaded portion 21 followed by a second cylindrical portion 25 with an external diameter slightly smaller than that of the first cylindrical portion 24. From the first cylindrical portion to the free end, a plurality of longitudinal engagement ribs 26 extend that are configured to engage the corresponding longitudinal grooves 15 in the head 12 of the bone anchoring element. The longitudinal engaging grooves and ribs form a form fit engagement structure. It shall be noted that any other form fit engagement structure between the bone anchoring engagement portion 23 and the coaxial recess 14 of the bone anchoring element may be contemplated, such as, for example, a hexagon-shaped connection or an other polygon structure.

As depicted in particular in FIGS. 6 and 7, a coaxial cylindrical blind hole 27 extends from the free end 29 of the bone anchoring element engagement portion 23 into the bone anchoring element engagement portion 23. The inner diameter of the blind hole 27 is slightly smaller than the inner diameter of the blind hole 16 in the bone anchoring element.

Referring in particular to FIGS. 8 and 9, a connection element in the form of a slotted pin 6 is provided that serves for connecting the bone anchoring element engagement portion 23 to the head 12 of the bone anchoring element 1. The slotted pin 6 comprises a cylindrical first portion 61 with an outer diameter that matches the inner diameter of the blind hole 27 of the bone anchoring element engagement portion 23 of the instrument. A free end 62 of the first portion 61 may be bevelled to facilitate the insertion into the blind hole 27. Adjacent to the first portion 61, there is a second portion 63 with a bevelled free end 64 and a slot 65 that extends from the free end 64 through approximately the whole length of the second portion 63. The slot 65 extends in a transverse direction through the whole pin thereby providing two cylinder segments 66a, 66b. The size of the slot 65 is such that the two cylinder segments 66a, 66b can be pressed towards each other to close the slot 65. A bottom 67 of the slot may be shaped as a substantially cylindrical segment-shaped recess with a transversely extending cylinder axis and a size sufficient to allow the movement of the two segments 66a, 66b. By means of the slot 65 the second portion 63 of the pin 6 is rendered resilient, so that it can exert an outwardly directed clamping force. Hence, an outer diameter of the second portion 63 is such that when the segment 66a, 66b are pressed together, pin 6 can be introduced with the second portion 63 into the blind hole 16 of the head 12 of the bone anchoring element 1. While the first portion 61 of the pin 6 is connected in a press-fit manner to the blind hole 27, the portion 63 firmly clamps the bone anchoring element 1 when it is inserted into the blind hole 16. The outer diameter of the second portion is slightly larger than the outer diameter of the first portion, so that at the transition between the second portion 63 and the first portion 61 a shoulder 68 is formed that acts as a stop when the pin 6 is inserted into the blind hole 27. Preferably, the slotted pin 6 is made of a highly elastic material, such as, for example, a superelastic NiTi alloy, for example Nitinol in the superelastic state. The pin 6 may be pre-assembled with the bone anchoring element engagement portion 23 of the instrument, as shown in FIG. 8.

Referring in particular to FIGS. 2 to 5, 10 and 11, the cutting member 4 comprises a first end 41 and an opposite second end 42. Adjacent to the first end 41, a substantially cylindrical portion 43 is provided the outer diameter of which is such that the first portion 43 is substantially flush with the central shaft portion 2 when the cutting member 4 is attached to the front portion 20 of the instrument. Between the first portion 43 and the second end a second portion 44 forms the cutting portion. A maximum outer diameter D of the cutting portion 44 corresponds to or is larger than an outer diameter of a receiving part of a polyaxial bone anchor at least in a region of a bottom end of the receiving part.

The cutting portion comprises a plurality of longitudinally extending flutes 45 or ribs that are slightly twisted with respect to the rotational axis R such that they are configured to cut bone material when the instrument the cutting member is rotated. The flutes 45 have a substantially trapezoidal cross-section in a plane perpendicular to the axis of rotation R. In the embodiment shown, the instrument is configured to be rotated in the clockwise direction corresponding to the thread direction of the bone screw.

A threaded bore 46 extends through the cutting member 4 from the first end 41 in direction of the second end 42. Adjacent to the threaded bore 46, there is a widened hollow cylindrical section 47 with a larger diameter that is configured to accommodate a part of the threaded front portion 21 of the instrument therein. Following the widened section 47, there is a narrowed hollow section 48 with a smaller inner diameter that is configured to accommodate the first portion 24 of the bone anchoring element engagement portion 23 therein. Between the second end 42 and the narrowed portion 48, an accommodation section 49 is provided that is formed by a cylindrical bore with a diameter that matches the largest outer diameter d of the head 12.

At the transition of the accommodation section 49 and the narrowing section 48, a stop 49a is formed that acts as an abutment for the free end surface 13 of the head 12.

An axial length of the accommodation section 49 is sized such that the whole spherical segment-shaped head 12 can be accommodated therein, while the shank 11 of the bone anchoring element 1 extends outside of the accommodation section 49. Hence, as can be seen in FIG. 6, when the bone anchoring element 1 is mounted to the instrument with the cutting member 4, the bone anchoring element 1 together with the cutting member 4 has substantially the same outer dimensions as the polyaxial bone anchor. Furthermore, an axial length of the cutting portion 44 might be the same or slightly larger than an axial length of a receiving part of the polyaxial bone anchor.

Figure 12:
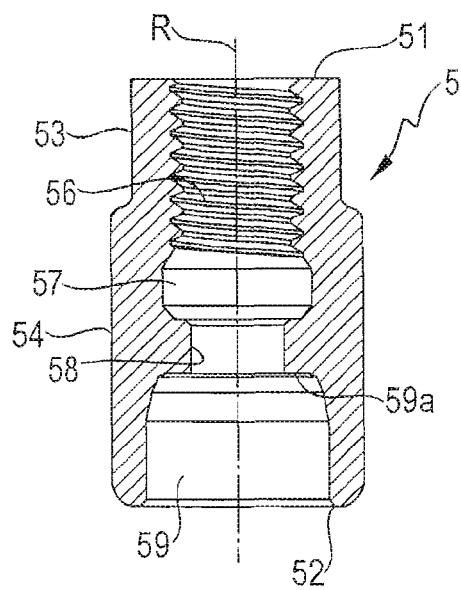
FIG. 12 shows a cross-sectional view of the holding sleeve, the cross-section taken in a plane containing the central longitudinal axis of the holding sleeve.
Figure 11:
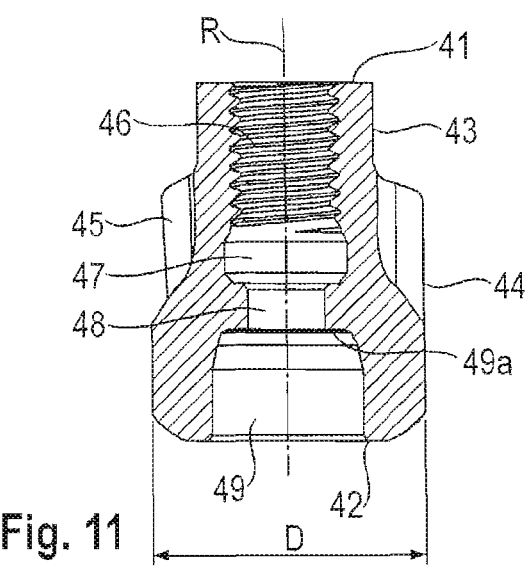
FIG. 11 shows a cross-sectional view of the cutting member along line A-A in FIG. 10.

Referring in particular to FIGS. 3, 5 and 12, the holding sleeve 5 comprises a first end 51, a second end 52, first portion 53 adjacent to the first end that has an outer diameter similar to the outer diameter of the first portion 43 of the cutting member. A second portion 54 is provided between the first portion 53 and the second end 52, which is substantially cylindrical with an outer diameter that is smaller than a maximum outer diameter of the cutting member 4. Therefore, the holding sleeve 5 has a smaller size in a radial direction that makes it useful for applications in which a cutting is not necessary and that might be more easily accessed with the instrument because of the smaller radial dimensions. Inside, the holding sleeve comprises sections correspond to the previously described inner sections of the cutting member 4, that means a threaded bore 56, a widened hollow section 57, a narrowing section 58 and an accommodation section 59 with an end stop 59a. With this design, the holding sleeve 5 can be used interchangeably with the cutting member 4.

All parts and portions of the instrument that are configured to engage tissue and/or bone and the bone anchoring element are made of a body compatible material, such as a body compatible metal, for example, Titanium or stainless steel or a body compatible alloy, such as Nitinol or of a body compatible plastic material, such as PEEK (Polyetheretherketone). The parts may be all of the same or of different materials.

Figure 13:
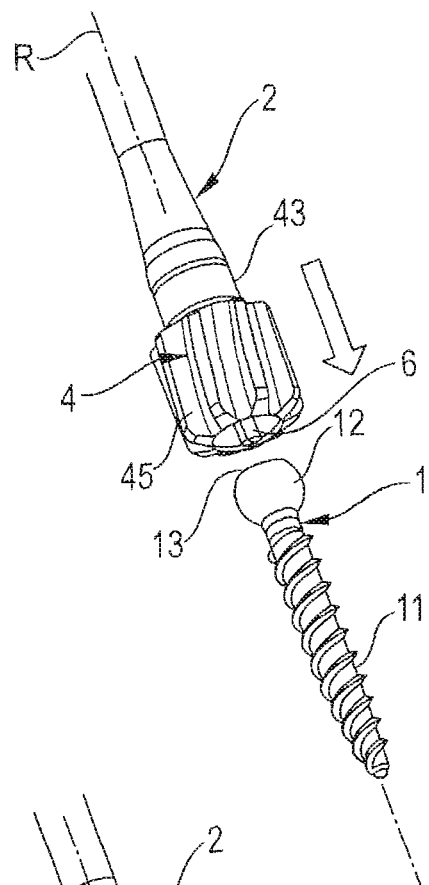
FIG. 13 shows a perspective view of a first step of use of the instrument, wherein the bone screw is to be mounted to the instrument.
Figure 14:
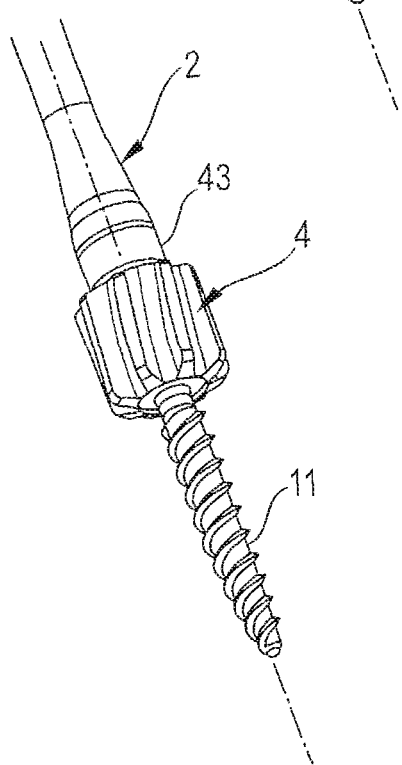
FIG. 14 shows perspective view of a second step of use wherein the bone screw has been mounted to the instrument and is ready for implanting.

A method of use of the instrument with the cutting member will be explained with reference to FIGS. 13 to 16. In a first step, the instrument and the bone anchoring element 1 are assembled. As shown in FIGS. 13 and 14, the head 12 of the bone anchoring element 1 is inserted into the accommodation section 49 of the cutting member 4 until the free end surface 13 of the head 12 abuts against the stop 49a provided at the end of the accommodation section 49 of the cutting member 4. Thereby, the slotted pin 6 engages with its second portion 63 the blind hole 16 of the bone anchoring element 1. The segments 66a, 66b are pressed together when entering the blind hole 16 and the resilient force that acts on the segments results in a firm clamping of the bone anchoring element 1. Simultaneously, the bone anchoring element is aligned with the axis of rotation R of the instrument.

When the head 12 is fully inserted into the cutting member 4 until its free end surface 13 abuts against the stop 49a, the shank 11 protrudes from the second end 42 of the cutting member in a similar way as if the bone anchoring element is mounted to a receiving part of polyaxial bone anchor. Therefore, the cutting member can generate the space for the receiving part and the bone anchoring element is placed in an optimized position with respect to the receiving part to be mounted later.

Figure 15:
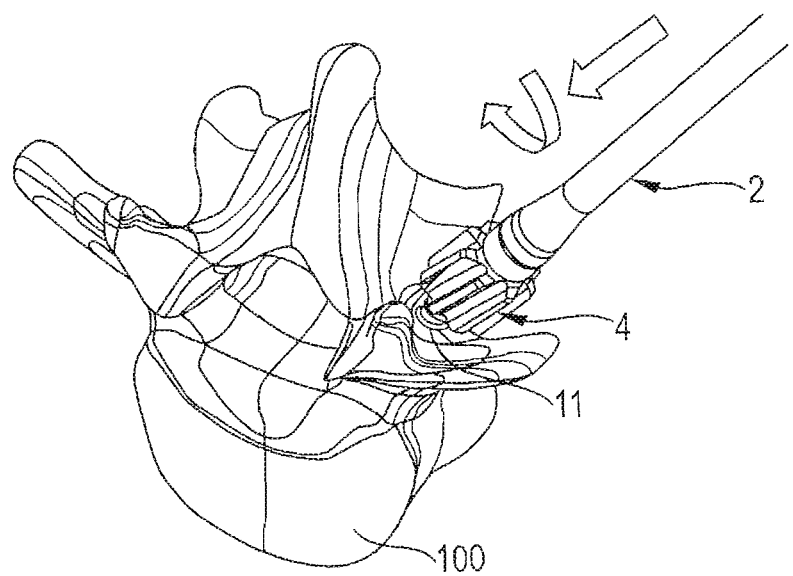
FIG. 15 shows a perspective view of further step of use, wherein the bone screw is inserted into a pedicle of a vertebra by rotating the instrument and wherein the cutting member cuts bone material in the surroundings of the implantation site.

Thereafter, the system of the instrument and the bone anchoring element is inserted into a pedicle of a vertebra 100 as can be seen in FIG. 15. When the shank 11 of the bone anchoring element 1 is advanced into the pedicle, the cutting flutes 45 of the cutting member 4 contact the surrounding bone material and cut away bone material that would be an obstacle for the receiving part of the polyaxial bone anchor that is to be mounted later. Hence, the instrument functions as an insertion and reaming instrument. The pin 6 firmly holds the anchoring element 1 in the instrument and acts not only as a connection element but also as an aligning and retaining element. Hence, wobbling of the anchoring element does not occur because the central axis of the pin, the screw axis and the axis of rotation of the instrument coincide.

Figure 16:
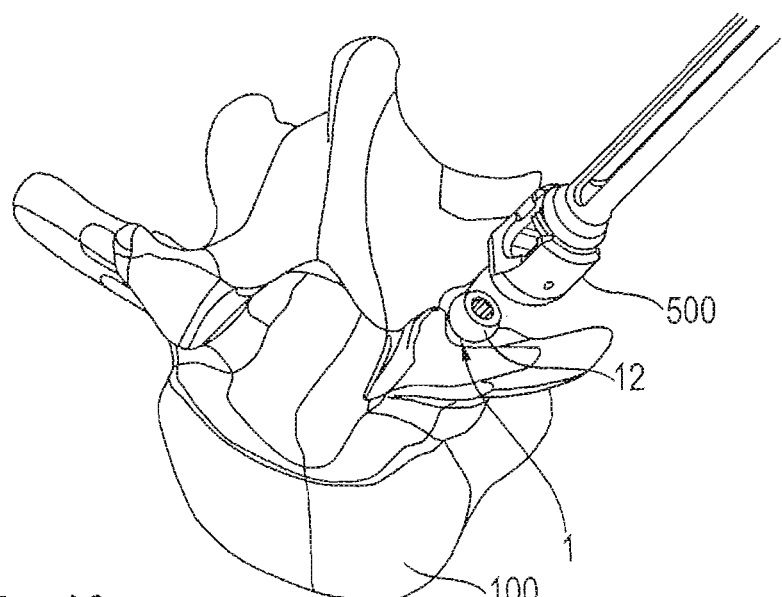
FIG. 16 shows perspective view of a step of attaching the receiving part of a polyaxial bone anchor to the inserted bone screw element after the instrument has been removed from the head of the bone screw.
Figure 17:
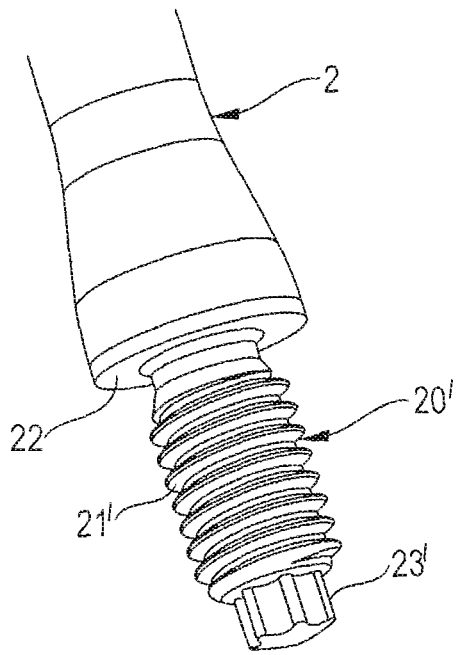
FIG. 17 shows a perspective view of an enlarged front portion of the instrument according to a second embodiment.
Figure 18:
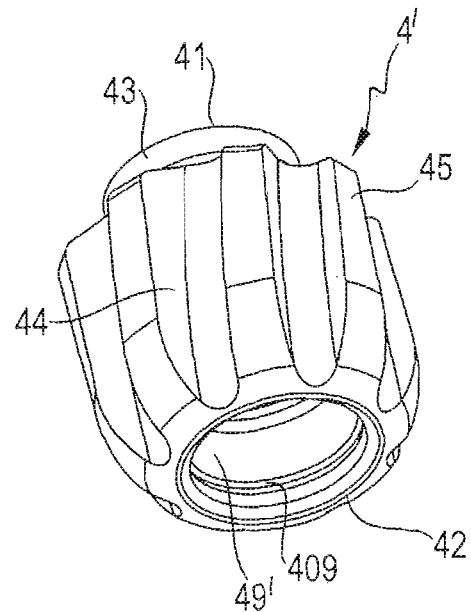
FIG. 18 shows a perspective view of the cutting member of the instrument according to the second embodiment.
Figure 19:
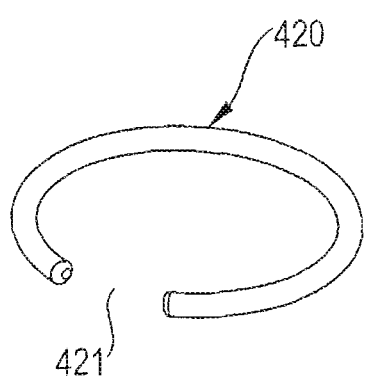
FIG. 19 shows a perspective view of the slotted ring of the instrument of the second embodiment.
Figure 20:
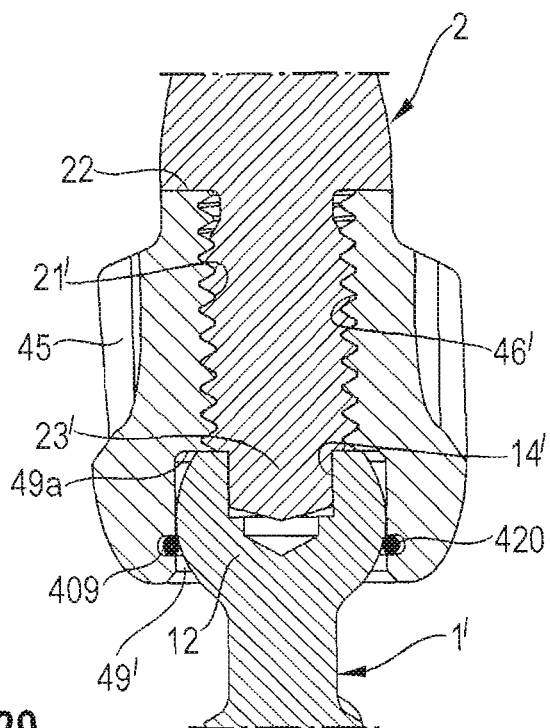
FIG. 20 shows a cross-sectional view of the front portion of the instrument according to the second embodiment with the cutting member mounted to the bone screw using the slotted ring, the cross-section taken in a plane containing the central longitudinal axis of the shaft of the instrument and the bone screw.

After the bone anchoring element 1 has been fully inserted into the pedicle so that only the head 12 and possibly a portion of the shank adjacent to the head 12 protrude out of the bone surface, the instrument is detached and a receiving part 500 of a polyaxial bone anchor is mounted onto the head, as depicted in FIG. 16.

Referring to FIG. 17 to 20, a second embodiment of the instrument will be explained. Parts and portions that are identical to the previous embodiments are marked with the same reference numerals and the description thereof will not be repeated. The instrument is particularly applicable to be used with a bone anchoring element 1' that has a conventional tool engagement recess 14' at its free end surface 13. The tool engagement recess 14' can be, for example, a torx-shaped recess or a hexagon-shaped recess. The front portion 20' of the instrument comprises a threaded front portion 21' as in the first embodiment and a bone anchoring element engagement portion 23' protruding from the threaded front portion 21' that is shaped so as to match the shape of the tool engagement portion 14'.

The cutting member 4' differs from the cutting member 4 of the first embodiment in that it comprises a threaded coaxial bore 46' that extends from the first end 41 up to the accommodation section 49' for the head. The accommodation section 49' for the head comprises at a position that is nearer to the second end 42 than to the abutment 49a an annular groove 409 that is configured and sized to accommodate a connection element therein. The connection element is formed as a slotted ring 420, as can be seen in particular in FIG. 19. The slotted ring 420 has in the example shown a circular cross section and a relatively large slot 421 that renders the slotted ring resilient in a radial direction. A size of the slotted ring 420 is such that by compressing the slotted ring 420 in a radial direction it can be introduced into the accommodation section 49' and placed partially into the groove 409 such that is still extends into the accommodation section 49'. When the head 12 is inserted, the slotted ring 420 is expanded by increasing the width of the slot 421 so that it extends deeper into the groove. The resulting resilient force that is exerted from the slotted ring onto the head 12 clamps the head 12 within the accommodation section 49' of the cutting member 4'. The alignment of the head 12 in the straight position is effected by the slotted ring 420. The slotted ring 420 is therefore, not only a connection but also an aligning and retaining element. Similar to the pin 6 of the first embodiment, the slotted ring 420 is preferably made from a superelastic NiTi alloy, such as Nitinol.

Use of the system of the instrument and the bone anchoring element 1' is similar to that of the first embodiment.

Figures 21, 22:
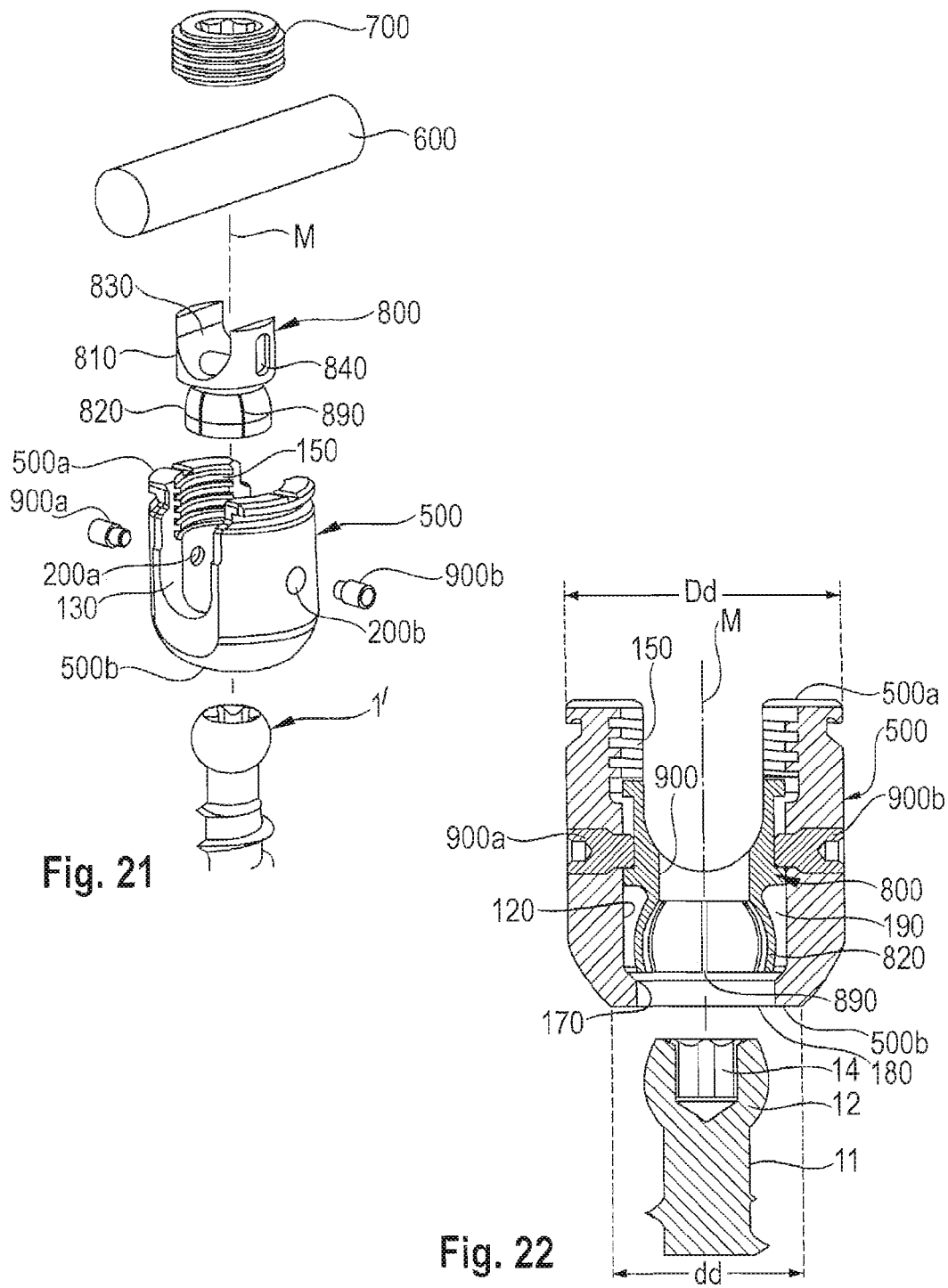
FIG. 21 shows a perspective exploded view of a polyaxial bone anchor that is suitable for use with the instrument.
FIG. 22 shows a cross-sectional view of the polyaxial bone anchor in a condition, in which the anchoring element is to be inserted into the receiving part.

A polyaxial bone anchor that can be used with the instrument will be described with reference to FIGS. 21 and 22. The polyaxial bone anchor shown in FIGS. 21 and 22 is an example for a bottom loading polyaxial bone anchor. It shall be understood that other polyaxial bone anchors can be used with the instrument. The bone anchoring element 1' is a bone anchoring element as shown in the second embodiment described above. The polyaxial bone anchor comprises the receiving part 500 for a receiving a rod 600 to connect the rod 600 to the bone anchoring element 1'. Further, a closure element 700 in the form of an inner screw is provided for securing the rod 600 and the receiving part 500. In addition, the polyaxial bone anchor includes a pressure element 800 for locking the head 12 in the receiving part 500. The pressure element 800 is held in the receiving part 500, for example, via pins 900a, 900b.

The receiving part 500 comprises a top end 500a and an opposite bottom end 500b in an axis of symmetry M passing through the top end 500a and bottom end 500b. A bore 120 is provided which is coaxial with the axis of symmetry M. In a first region adjacent to the top end 500a, the receiving part 500 has a U-shaped recess 130, which is symmetric with respect to the axis of symmetry M, the recess 130 having a bottom directed towards the second end 500b. Adjacent or near to the top end 500a an internal thread 150, which cooperates with the inner screw 700, is provided. A channel formed by the U-shaped recess 130 is sized so as to receive the rod 600 therein, which shall connect a plurality of anchoring devices. Near to the bottom end 500b, the bore 120 comprises a narrowing section 170 that tapers towards the bottom end 500b. An opening 180 is provided at the bottom end 500b. A diameter of the opening 180 is larger than a diameter of the head 12, so that the head is insertable through the bottom end, and smaller than the inner diameter of the bore 120. The coaxial bore 120 provides an accommodation space 190 for the screw head 12.

The pins 900a, 900b are insertable into corresponding transverse bores 200a, 200b, that are located each at 90° offset from the channel axis in the side walls of the receiving part 500.

The pressure element 800 includes a first portion 810, which is substantially cylindrical and which has an outer diameter slightly smaller than the inner diameter of the bore 120, so that the pressure element 800 is movable in the bore 120. It further comprises a second portion 820 which is recessed with respect to the first portion and which has a maximum outer diameter smaller than the inner diameter of the bore 120. The first portion 810 has its end opposite to the second portion 820 a U-shaped recess 830 for receiving the rod 600 therein when the pressure element 800 is located in the receiving part 500. At the lateral side of the U-shaped recess 830, the pressure element comprises two elongate recesses 840 in the outer wall which are arranged opposite to each other and which are aligned such that a longer side of the elongate recess 840 is parallel to the axis of symmetry M of the receiving part 500.

The second portion 820 is formed similar to a cap and comprises slits 890, that are open towards the lower rim and provide flexibility to the second portion. The size of the cap-like portion 820 may be such that the cap-like portion 820 can snap onto the head 12.

The receiving part 500 comprises an outer diameter Dd in a region of the channel which may decrease towards the second end 500b to an outer diameter dd at the bottom end 500b. The outer diameter D of the cutting member 4, 4' of the instrument is equal to or greater than the outer diameter dd of the receiving part at the bottom end of the receiving part.

The bone anchoring element 1' can be inserted from the bottom end 500b into the receiving part 500. Usually, the pressure element 800 is pre-assembled with the receiving part 500 and held in alignment with the channel axis by the pins 900a, 900b that extend through bores 200a, 200b into the elongate recesses 840, 840. When the head 12 enters the receiving part from the bottom end, it enters the cap-like portion 820 of the pressure element which can spread due to the slits 890 and due to the space provided by the accommodation space 190 of the bore 120. Once the cap-like portion 820 of the pressure element 800 has been placed onto the head 12, the rod 600 can be inserted. By tightening the closure element 700, the pressure element 800 is moved downward so that the cap-like portion 820 enters the narrowed portion of the bore 120 and clamps the head. Final tightening of the inner screw 700 locks the head.

A system of the instrument and a bone anchoring element includes a bone anchoring element as described in the embodiments before and a corresponding instrument. A system of the instrument and a polyaxial bone anchor includes the instrument according to the embodiments described before and any polyaxial bone anchor that comprises a receiving part that pivotably receives the bone anchoring element, preferably, a bottom loading polyaxial bone anchor, one example of which is shown in FIGS. 21 and 22.

Modifications of the embodiment described before may be contemplated. For example, the cutting member can be fixed and is not detachable. Also, the central shaft portion and the front portion of the instrument can be provided in one piece with a cutting member with an outer diameter corresponding to an outer diameter of the receiving part. The described connections between the bone anchoring element and the instrument can be made otherwise without departing from the scope of the invention.

For the bone anchoring element, all kinds of anchoring elements can be used and combined with the instrument and/or the receiving part. These anchoring elements are e.g. screws of different length, with different diameters, cannulated screws, screws with different thread forms, nails hooks, etc. The head and the shank may also be separate parts that are connectable to each other.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring system comprising:
    a cutting member comprising a tubular body and a plurality of cutting portions, each of the plurality of cutting portions extending along the tubular body and having a cutting edge configured to cut bone material;
    a shaft having a front portion having an end portion, the front portion being configured to engage and transfer torque to the cutting member, and a longitudinal axis of the shaft defining an axis of rotation; and
    a bone anchoring element comprising a shank and a head, the shank being configured to anchor the bone anchoring element into bone,
    wherein the cutting member is configured to receive the end portion of the shaft inside the tubular body,
    wherein the end portion of the shaft is configured to engage and transfer torque to the head, and
    wherein each cutting edge extends along a cutting axis, the cutting axis of one cutting edge being offset from the cutting axis of another cutting edge.

2. The system of claim 1, wherein the plurality of cutting portions are longitudinally extending flutes that are twisted relative to the longitudinal axis.

3. The system of claim 1, wherein a first inner portion of the tubular body extending from a second end of the cutting member has a diameter greater than that of a second inner portion of the tubular body adjacent to the first inner portion.

4. The system of claim 3, wherein a surface parallel to the longitudinal axis and between the first inner portion and the second inner portion of the tubular body is flat.

5. The system of claim 4, wherein the end portion of the shaft is configured to extend into the first inner portion of the tubular body from a first end of the tubular body opposite to the second end.

6. The system of claim 1, further comprising a connection element configured to be connected to the shaft or the cutting member.

7. The system of claim 6, wherein the connection element is a pin,
    wherein a distal end of the shaft has a recess extending from the distal end along the longitudinal axis of the shaft, and
    wherein a first portion of the pin has a diameter that is substantially the same as that of the recess in the shaft.

8. The system of claim 7, wherein a second portion of the pin has a slot extending from an end of the pin toward the first portion of the pin.

9. The system of claim 8, wherein a portion of the slot closest the first portion of the pin has a width greater than that of another portion of the slot.

10. The system of claim 6, wherein the connection element is a slotted ring,
    wherein an inner portion of the tubular body adjacent to a second end of the tubular body has a groove, and
    wherein the groove is configured to accommodate the slotted ring.

11. The system of claim 1, wherein the cutting member is configured to be connected to and detached from the shaft.

12. The system of claim 11, wherein the cutting member and the shaft are configured to be connected by a threaded connection having a thread direction corresponding to a cutting direction of the cutting edges.

13. The system of claim 12, further comprising a sleeve member configured to be connected to the shaft by the threaded connection instead of the cutting member in an interchangeable manner,
    wherein the sleeve member has a smooth outer surface and has an outer diameter smaller than that of the cutting member.

14. The system of claim 1, wherein the bone anchoring element is a bone screw, and
    wherein the bone anchoring element comprises a threaded shank and a spherical segment-shaped head.

15. A bone anchoring system comprising:
    a shaft having a front portion having an end portion, a longitudinal axis defining an axis of rotation;
    a cutting member configured to be coupled to the front portion and comprising a plurality of cutting portions; and
    a polyaxial bone anchor comprising a bone anchoring element and a receiving part, the bone anchoring element comprising a shank and a head, the shank being configured to anchor the bone anchoring element into bone,
    wherein the end portion of the shaft is configured to engage and transfer torque to the head,
    wherein the cutting member is configured to accommodate the head at an inner space of the cutting member,
    wherein the receiving part has a top end and an opposite bottom end, a channel configured to receive a rod, and a seat configured to pivotably receive the head of the bone anchoring element at the bottom end of the receiving part,
    wherein the bottom end of the receiving part has an opening that is larger than an outer diameter of the head, and
    wherein an outer diameter of the cutting portions of the cutting member is equal to or larger than an outer diameter of the bottom end of the receiving part.

16. An instrument for inserting a bone anchoring element comprising:
- a cutting member comprising a tubular body and a plurality of cutting portions protruding from and extending along the tubular body, each of the plurality of cutting portions having a cutting edge configured to cut bone material; and
- a shaft having an end portion configured to engage and transfer torque to the cutting member, and a longitudinal axis defining an axis of rotation,
- wherein the cutting member is configured to receive the end portion of the shaft inside the tubular body, and
- wherein a first inner portion of the tubular body extending from a second end of the cutting member is configured to accommodate a head of a bone anchoring element and has a diameter greater than that of a second inner portion of the tubular body adjacent to the first inner portion.

17. A method for inserting a bone anchor into a bone utilizing a bone anchoring system, the bone anchoring system comprising a shaft having a front portion having an end portion and a longitudinal axis defining an axis of rotation; a cutting member coupled to the shaft and comprising a plurality of cutting portions; and a polyaxial bone anchor comprising a bone anchoring element and a receiving part, the bone anchoring element comprising a shank and a head, the shank being configured to anchor the bone anchoring element into bone, wherein the end portion of the shaft is configured to engage and transfer torque to the head, wherein the cutting member is configured to accommodate the head at an inner space of the cutting member, wherein the receiving part has a top end and an opposite bottom end, a channel configured to receive a rod, and a seat configured to pivotably receive the head of the bone anchoring element at the bottom end of the receiving part, wherein the bottom end of the receiving part has an opening that is larger than an outer diameter of the head, and wherein an outer diameter of the cutting portions of the cutting member is equal to or larger than an outer diameter of the bottom end of the receiving part, the method comprising:
- inserting the bone anchoring element into a bone;
- cutting the bone with the cutting member while further inserting the bone anchoring element; and
- retracting the shaft and the cutting member.

18. The method of claim 17, further comprising coupling the head of the bone anchoring element to both the cutting member and the end portion of the shaft prior to the inserting the bone anchoring element.

19. The method of claim 17, further comprising:
- mounting the receiving part onto the head of the bone anchoring element;
- inserting a rod into the channel of the receiving part; and
- advancing a closure element in the channel of the receiving part towards the bottom end of the receiving part to advance a pressure element around the head.

20. The method of claim 17, wherein the bone anchoring system further comprises a sleeve member coupled to the shaft instead of the cutting member, and
wherein the sleeve member has a smooth outer surface.

* * * * *